(12) United States Patent
Kondoh

(10) Patent No.: US 7,407,933 B2
(45) Date of Patent: Aug. 5, 2008

(54) DRUG CONTAINING ANGIOTENSIN CONVERTASE

(76) Inventor: Gen Kondoh, 18, Okazaki Kitagosho-machi, Sakyo-ku, Kyoto-shi, Kyoto (JP)

( * ) Notice: Subject to any disclaimer, the term of this patent is extended or adjusted under 35 U.S.C. 154(b) by 397 days.

(21) Appl. No.: 10/532,986

(22) PCT Filed: Oct. 29, 2003

(86) PCT No.: PCT/JP03/13851

§ 371 (c)(1),
(2), (4) Date: Jun. 27, 2005

(87) PCT Pub. No.: WO2004/039396

PCT Pub. Date: May 13, 2004

(65) Prior Publication Data

US 2006/0239993 A1      Oct. 26, 2006

(30) Foreign Application Priority Data

Oct. 29, 2002   (JP) .............................. 2002-314078

(51) Int. Cl.
*A61K 38/48*       (2006.01)
*C12N 9/64*        (2006.01)

(52) U.S. Cl. ...................... 514/12; 530/350; 424/94.63; 435/226

(58) Field of Classification Search ............... 424/94.63; 435/226; 530/350; 514/12
See application file for complete search history.

(56) References Cited

FOREIGN PATENT DOCUMENTS

| JP | 2001-316287 | 11/2001 |
|---|---|---|
| WO | 91/00354 | 1/1991 |
| WO | 95/32725 | 12/1995 |

OTHER PUBLICATIONS

Sen et al., J. Biol. Chem. 268, 25748-25754 (1993).*
Chemical Abstract, 1995, vol. 123, Abstract No. 330713, abstract & A. Israel et al., "Angiotensin II receptor subtypes and phosphoinositide hydrolysis in rat adrenal modulla", Brain Research Bulletin, 1995, vol. 38, No. 5, pp. 441-446.
Chemical Abstract, 1993, vol. 118, Abstract No. 252487, abstract & M. Raizada et al., "Increased angiotensin II type-1 gene expression in neuronal cultures from spontaneously hypertensive rats", 1993, vol. 132, No. 4, pp. 1715-1722.
Chemical Abstract, 1989, vol. 113, Abstract No. 126431, abstract & A. J. Robinson-White et al., "Inhibition of inositol phospholipid hydrolysis in endothelial cells by pentobarbital", European J. Pharmacol., Molecular Pharmacology Section, 1989, vol. 172, No. 3, pp. 291-303.
G. Kondoh et al., "Angiotensin-converting enzyme is a GPI-anchored protein releasing factor crucial for fertilization", Nature Medicine, vol. 11, No. 2, pp. 160-166, Feb. 2005.
H. Kondo, "Mouse Seishoku Saibo GPI Anchor-gata Tanpakushitsu Yuri Inshi no Tanri to Kino Kaiseki" Seishoku Saibo no Seigyo Kiko to Hassei Kogaku, Heisei 11-14, Nendo, No. 11234101, pp. 69-72, (2003), English translation.
E. Jaspard et al., "Differences in the properties and enzymatic specificities of the two active sites of angiotensin I-converting enzyme (kininase II). Studies with bradykinin and other natural peptides", J. Biol. Chem., 1993, vol. 268, No. 13, pp. 9496-9503.
L. Wei et al., "The two homologous domains of human angiotensin I-converting enzyme are both catalytically active", J. Biol. Chem., 1991, vol. 266, No. 14, pp. 9002-9008.
L. Wei et al., "The two homologous domain of human angiotensin I-converting enzyme interact differently with competitive inhibitors", J. Biol. Chem., 1992, vol. 267, No. 19, pp. 13398-13405.
S. Pang et al., "Roles of the juxtamembrane and extracellular domains of angiotensin-converting enzyme in ectodomain Shedding", Biochem. J., 2001, vol. 358, (Pt 1), pp. 185-192.
B. Maric et al., "Replacement of the transmembrane anchor in angiotensin I-converting enzyme (ACE) with a glycosylphosphatidylinositol tail affects activation of the B2 bradykinin receptor by ACE inhibitors", J. Biol. Chem., 2000, vol. 275, No. 21, pp. 16110-16118.
S. Pang et al., "The ectodomain of angiotensin converting enzyme does not dictate sensitivity to sacretase cleavage", Biochemical Society transactions, 2000, vol. 28, No. 5, p. A262.

* cited by examiner

*Primary Examiner*—Chih-Min Kam
(74) *Attorney, Agent, or Firm*—Wenderoth Lind & Ponack, L.L.P.

(57) ABSTRACT

The medicine containing angiotensin-converting enzyme or its peptidase-inactivated mutants that specifically releasing GPI-anchored proteins from the cell surface, for preventing or curing diseases, such as prion-related diseases, inflammatory diseases, bacterial infectious diseases and male infertility due to sperm-egg binding insufficiency.

5 Claims, 13 Drawing Sheets

- ● : phosphate
- ● : ethanolamine

DRUG CONTAINING ANGIOTENSIN CONVERTASE

This application is a U.S. national stage of International Application No. PCT/JP2003/013851 filed Oct. 29, 2003.

TECHNICAL FIELD

This application relates to the invention of angiotensin-converting enzyme containing medicine. In detail, the invention of this application relates to a medicine that is useful for prevention and treatment of diseases such as prion-related diseases, bacterial infectious diseases and male infertility by releasing GPI-anchored proteins from cell membrane.

BACKGROUND ART

The angiotensin-coverting enzyme [ACE, dipeptidylcarboxypeptidase (EC 3.4.15.1)] is a member of rennin-angiotensin system regulating blood pressure. It is known that ACE leads some physiological changes (blood pressure elevation, for example) by converting angiotensin I to active angiotensin II and inactivating bradyskinin (Non-patent Document 1). So, there are so many inventions about medicine (blood pressure-lowering drug, for example) of which action mechanism is down regulation of blood pressure by inhibiting ACE (Patent Documents 1-4).

The cell membrane is consisted with proteins and lipids, where many biological processes, such as energy production, signal transduction, cell-to-cell interaction and secretion, take place. The GPI-anchored protein is a main component of cell membrane, which bounds there via GPI-anchor, crucial for many biological processes. However, the normal prion protein also binds the GPI-anchor and when the pathogenic form of prion binds to the normal counterpart, prion-related diseases such as Creutzfeldt-Jakob disease, Gerstmann-Straussele syndrome and kuru disease, may occur. A bacterial toxin, lipopolysaccharide (LPS) binds to its receptor CD14, which is also a GPI-anchored protein, and exhibits cytotoxicity.

In addition, when the sperm binds to zona pellucida of egg, GPI-anchored proteins (ex. PH-20 and TESP5 in mouse; Non-patent Documents 2, 3) should be released from the sperm surface and, if not, male infertility might occur.

The release of GPI-anchored protein from the cell surface is effective for relieving or curing prion-related diseases, bacterial infection and some kind of male infertility. As a protein showing GPI-anchor-cleaving activity (GPIase activity), GPI-PLD is only enzyme known so far in mammals. However, GPI-PLD has been reported to exhibits the GPIase activity only when it is expressed intracellularly in culture cells (Non-patent Document 4). Therefore, GPI-PLD might not be useful as medicine in the light of use of GPIase activity for medication.

It has been reported that ACE cleaves numbers of substrates other than angiotensin I and bradykinin, such as enkephalin and pre-enkephalin such as heptapeptide and octapeptide. Further, ACE is known to hydrolyze tridecapeptide and neurotensin, as well as to inactivate substance P by digesting. However, the GPI-anchored protein releasing activity of ACE has never been reported.

Patent Document 1: JP10-036391 A

Patent Document 2: JP2001-064299 A

Patent Document 3: JP2001-233789 A

Patent Document 4: JP2002-138100 A

Non-patent Document 1: Hooper et al., Int. J. Biochem. 23:641-647, 1991

Non-patent Document 2: Honda et al., J. Biol. Chem. 277: 16976-16984, 2002

Non-patent Document 3: Lin et al., J. Cell Biol. 125:1157-1163, 1994

Non-patent Document 4: Tujioka et al., Biochem. Biophys. Res. Commun. 251:737-747, 1998

Non-patent Document 5: Skidgel et al., Neuropeptides and Their Prptidases, Turner A J Ed., Chichester, UK, 1989

DISCLOSURE OF INVENTION

The present inventor has searched for molecules that exhibit GPI-anchored protein releasing activity and found ACE be one of such molecules.

This invention owes to such novel findings by the inventor, and a subject of this invention is to provide novel medicine that may prevent or cure such diseases by releasing harmful GPI-anchored proteins from the cell surface.

Regarding to ACE, numerous researches have been made for inhibiting ACE activity since the known physiological activities of ACE (for example, peptidase activity causing blood pressure elevation and the like) are harmful. As a novel medicine to be provide, another subject of this invention is to provide an ACE of which the harmful peptidase activity is inhibited and the only GPI-anchored proteins releasing activity is available.

To solve such subjects, this invention provides in angiotensin-converting enzyme containing medicine, of which action mechanism is release of GPI-anchored protein from the cell surface.

The medicine is preferably for preventing or curing prion-related diseases, bacterial infection or male infertility.

An embodiment of the medicine is that the angiotensin-converting enzyme is a mutant angiotensin-converting enzyme to which one or more amino acid mutation is introduced so that GPI-anchored protein releasing activity is maintained but peptidase activity is inactivated. Preferably, the mutant enzyme has one or more amino acid substitution in the sequence of His Glu Met Gly (the $413^{th}$ to $416^{th}$ amino acid residue of SEQ ID NO: 4), and most preferably, the mutant enzyme has Glu to Asp amino acid substitution in the sequence of His Glu Met Gly His (the $413^{th}$ to $417^{th}$ amino acid residue of SEQ ID NO: 4).

This invention also provides a mutant angiotensin-converting enzyme to which one or more amino acid mutation is introduced so that GPI-anchored protein releasing activity is maintained but peptidase activity is inactivated.

The mutant enzyme has one or more amino acid substitution, and preferably has Glu to Asp amino acid substitution in the sequence of His Glu Met Gly His (the $413^{th}$ to $417^{th}$ amino acid residue of SEQ ID NO: 4).

In this invention, "GPI-anchored protein" is defined as proteins that are bound to cell membrane via GPI-anchor, such as normal and pathogenic prion protein and CD14, the receptor for LPS etc.

"The releasing of GPI-anchored protein from the cell surface" means cleaving GPI-anchor from GPI-anchored proteins to inactivate their harmful functions. By this mechanism, normal prion protein is released from the cell surface to prevent accession of pathogenic prion protein, which binds to its normal counterpart and exhibits its pathogenecity. Moreover, CD14, the receptor for LPS, is released from the cell surface to prevent membranous CD14-LPS complex formation, which triggers cytotoxicity and enhances inflammation.

"The prion-related diseases" includes Creutzfeldt-Jakob disease, Gerstmann-Straussele syndrome and kuru disease etc.

"The bacterial infectious diseases" includes infectious diseases by Gram-negative bacteria, such as *Escherichia coli, Haemophilus influenzae, Salmonella typhimurium, Neisseria meningitis, Pseudomonas aerginosa* etc, and endotoxin shock induced by bacterial toxin.

"The male infertility" includes infertility developed by insufficiency of GPI-anchored proteins (TESP5, PH-20 etc.) release from the sperm surface on sperm-egg binding phase.

The general techniques for carrying out this invention could be referred to Remington's Pharmaceutical Sciences, 18th Edition, ed. A. Gennaro, Mack Publishing Co. Easton, Pa., 1990 for preparing drugs and Sambrook and Maniatis, in Molecular Cloning—A Laboratory Manual, Cold Spring Harbor Laboratory Press, New York, 1989 and Ausubel, F. M. et al., Current Protocols in Molecular Biology, John Wiley & Sons, New York, N.Y., 1995 for gene engineering and molecular biological techniques.

BEST MODE FOR CARRYING OUT THE INVENTION

Figure 1:
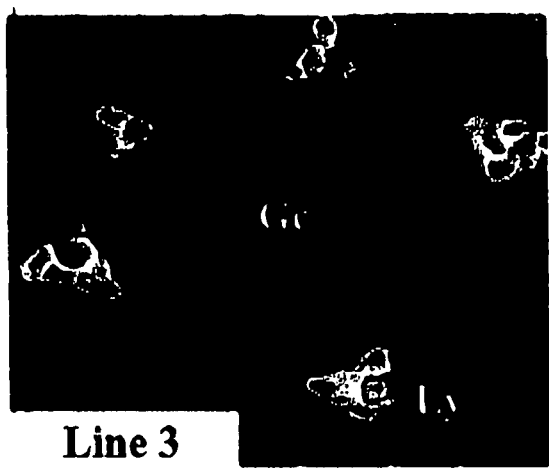
FIG. 1 shows localization of fluorescence in the testis of EGFP-GPI transgenic mouse observed by a microscopy. EGFP-GPI expression in germ cells (Gc) was solely observed in line 2 transgenic mice but not in line 1 and line 3 (data not shown). Ly. The Leydig cell. Magnification, ×200.
Figure 1:
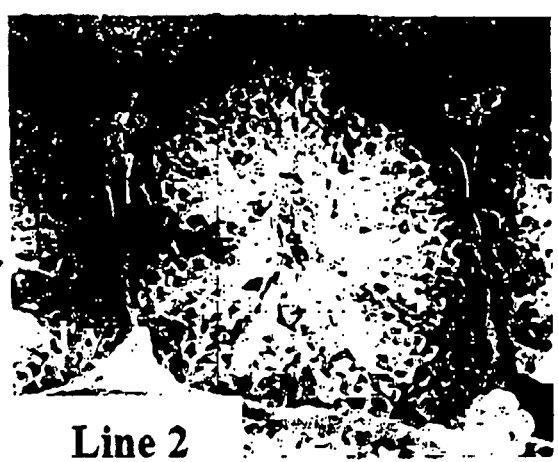

The ACE (somatic ACE-S and germinal ACE-T) usable in this invention could be prepared from mammalian (including human) cells or tissues by known methods. Moreover, commercially available sample (ex. ACE-S: Sigma A-6778 derived from rabbit lung) or angiotensin-coverting enzyme homologue disclosed in JP2002-525108 A. There reported numerous kind of ACE amino acid or polynucleotides (cDNA sequences) derived from various species, such as human ACE-S (GenBank/J04144), human ACE-T (GenBank/M26657), human ACE isoform 3 precursor (GenBank/NM_152831), human ACE isoform 2 precursor (GenBank/NM_152830), human ACE isoform 1 precursor (GenBank/NM_000789), human ACE-like protein (GenBank/NM_021804), mouse ACE-T (GenBank/NM_009598), mouse ACE-S (GenBank/XM_110936), rat ACE (GenBank/NM_012544), rat ACE-T (GenBank/AF539425), rabbit ACE-T (Swissprot/P22968), rabbit ACE-S (Swissprot/P12822), chicken ACE (GenBank/Q10751), bovine ACE (Swissprot/1919242A), fly ACE precursor (Swissprot/10715), fruit fly ACE (GenBank/NM_165070), that ACE sample used in this invention could also be developed from these published amino acid sequence by in vitro peptide synthesis, in vitro translation system, or some other host-expression vector systems for producing recombinant molecules. The polynucleotides of ACE, such as ACE cDNA, could also be obtained by screening established cDNA library or RT-PCR by using oligonucleotide probes synthesized from nucletide sequences published A GenBank or JP2002-525108 A, for example.

To produce ACE by in vitro translation, ACE polynucleotides described above were inserted in the vector carrying RNA polymerase promoter, such as pKA1, pCDM8, pT3/T7-18, pT3/T7-19, pBluescript II. RNA for ACE was produced by in vitro trancription using RNA polymerase, such as T7, T3, or SP6. These RNA molecules were incubated with rabbit reticrocyte lysate or wheat germ extract that contains materials for in vitro translation.

To produce ACE in prokaryotic cells such as *E. coli*, ACE polynucleotides described above were inserted in the vector carrying replication origin, promoter, ribosomal binding site, multiple cloning sites, and terminating site that could be worked in cognate prokaryotes. Recombinant protein products were extracted from cultured cells. For expressing ACE in *E. coli*, pUC, pBluescripts II, pET or pGEX systems could be used.

To produce ACE in eukaryotes, ACE polynucleotides described above were inserted in the vector carrying promoter, multiple cloning sites, splicing sequences, poly-A additional sequences, such as pKA1, pCDM8, pSVK3, pMSG, pSVL, pBK-CMV, EBV vector, pRS, pcDNA3, pYESs. Recombinant protein products were expressed in transformed cells. All eukaryotic cells could be avilable, while mammalian cells, such as COS7 and CHO, yeast cells, such as *Saccahromyces cereviciae*, and *Schizosaccahromyces pombe*, silkworm cells or *Xenopus laevis* oocytes are frequently used.

For introducing expression vectors in eukaryotic cells, methods such as electroporation, calcium-phosphate, liposome or DEAE-dextran systems could be utilized.

For purifying recombinant ACE products, procedures combining established methods, such as treatments with detergents, sonication, treatments with enzymes, salt precipitation, dialysis, centrifugation, limiting filtration, gel filtration, SDS-PAGE, isoelcctrofocusing gel electrophoresis, ion-exchanging chromatography, hydrophobic chromatography, affinity chromatography or reverse-phase chromatography, could be utilized.

As the ACE usable for this invention might be mutant ACE molecules that were inactivated for angiotensin-converting activity (peptidase activity for up-regulating blood pressure) but not GPI-anchored protein releasing activity. Because ACE has activity for up-regulating blood pressure, there may occur harmful side effect such as hypertension beside GPI-anchor releasing action when ACE was introduced in vivo. ACE mutants developed by substituting one or more amino acid residues in this invention are promising for reducing or removing such side effects, while maintaining the desirable main effect.

Based on the known ACE amino acid sequences (SEQ ID NO: 4, for example), mutant ACE molecules could be synthesized by the solid-phase polypeptide synthesis system (such as *Organic Syntheses Collective Volumes*, Gilman, et al. Eds. John Wiley & Sons, Inc., NY), or obtained as expression products from mutant polynucleotide produced by site-directed mutagenesis using PCR or Kunkel method (Kunkel, T. A. Proc. Natl. Acad. Sci. USA, 82: 488, 1985 or Kunkel, T. A. et al. Methods in Enzymology 154: 367, 1987). From the prepared peptides having various mutations, the desired mutant ACE could be obtained by confirming the peptidase activity and GPIase according to the tests as described below.

Although it would be possible to accordingly design the mutation introducing sites for preparing the mutant ACE, the present invention provide as a preferable one the mutant ACE that carries more than one amino acid substitutions in the amino acid sequence of His Glu Met Gly His (the 413rd-417th of SEQ ID NO: 4) in the ACE amino acid sequence. This sequence region consists zinc binding site necessary for peptidase activity and are almost completely conserved among the reported ACE, either ACE-T or ACE-S, from all species, such as mammalian (human, mouse, rat, rabbit, cow), avian (chicken) and insect (fly). The present invention further provides, as a more preferable one, a mutant ACE having Glu to Asp substitution in the sequence of His Glu Met Gly His (the 413$^{th}$ to 417$^{th}$ amino acid residue of SEQ ID NO: 4) (hereinafter, the mutant may be referred to as "peptidase inactivated ACE (E414D)").

For the medicine of this invention, the ACE could be used substantially solely, or preferably combined with pharmaceutically acceptable carrier in accordance with the kinds of diseases and drug-administration routs etc. Therefore, the medicine of this invention could be mixed with carriers to be a suitable formulation for oral or non-oral administration.

The non-oral administrations include topical injection, peritoneal injection, selective intra-venous administration, venous injection, subcutaneous injection, organ perfusion, or rectal administration, and such carrier as distilled water, salt solution, glucose solution, or a mixed solution of same and glucose solution could be used for injection medicine. The medicine could also contain such supplement as pH-adjusting buffer (sodium hydroxy phosphate, citric acid etc.), osmotic compounds (sodium chloride, glucose etc.) and preservatives (para oxy methyl benzoate, hydroxy propil benzoate etc.). These drugs could be sterilized by membrane filtration, addition of anti-microbial chemicals, irradiation of heating. The medicine could also be produced as a powder and dissolved in a solution at application.

An oral medicine could be produced in an appropriate form for gastrointestinal absorption, such as pill, capsule, granule, powder, suspension or syrup. Carriers for the oral medicines could be ordinal supplements, such as binder (syrup, Arabian gum, gelatin, sorbit, tragacanth, poly vinyl pyrrolidone, hydroxy propil cellulose, etc.), diluents (lactose, sugar, cornstarch, calcium phosphate, glycine, etc.), lubricants (Magnesium stearate, talc, poly ethylene glycol, silica, etc.), disintegrating agents (potato starch, carboxy methyl cellulose, etc.), or humectants (sodium lauryl sulfate, etc.). Flavor components such as strawberry flavor or peppermint might be available. Tablets could be coated in a usual procedure. Oral medicine could be produced in a solution or a dry product. Such oral medicine could contain preservatives such as methyl or propil p-hydroxybenzoate, sorbinate, etc.

Concentration of ACE in the medicine should be determined by type of diseases and the administration route. Usually, it should be 5-100% (w/w) or more preferably 10-60% (w/w).

The amount of medicine to be administered should be determined by age, body weight, symptoms or the administration route. Usually, it should be 100-200 mg/kg body weight/day. Since ACE is an endogenous protein of human, it might not have any problem in terms of safety.

EXAMPLES

As examples of this invention, results of examinations for ACE activities are described for explaining this invention in detail. However, this invention should not be restricted by these examples.

1. Materials and Methods 1.1. Histological Analysis

EGFP-GPI transgenic mice (Kondoh, G., et al. FEBS lett., 458, 299-303, 1999) were deeply anesthetized with phenobarbital and fixed with 4% (w/v) paraformaldehyde-PBS via the left ventricle of the heart. Excised tissues were fixed in 4% (w/v) paraformaldehyde-PBS and then incubated in 20% sucrose-PBS for 48 h at 4° C. Pieces of tissues were then embedded in Tissue-Tek O. C. T. compound (Sakura Finetek, Torrance, Calif.), quickly frozen with dry ice and sectioned on a cryostat in 5-10 μM thicknesses. Preparations were examined by fluorescence microscopy with GFP-specified filters (Olympus, Tokyo).

1.2. Lysate Preparation

Cells and tissues were first homogenized in TNE solution (10 mM Tris-HCl pH 7.8, 1 mM EDTA, 150 mM NaCl) with Complete protease inhibitor (Boehringer Mannheim, Mannheim, Germany) at an ice cold temperature. The homogenates were centrifuged at 100,000×g. The supernatants were collected and stocked (the water-soluble fraction). The precipitates were washed with TNE buffer and then homogenized in 1% Triton X-114 (Nacalai tesque, Kyoto)-TNE solution with Complete protease inhibitor and centrifuged at 100,000×g. The supernatants were collected and stocked (the detergent-soluble fraction). Sperm samples were incubated in TYH medium for 1 h to allow capacitation.

1.3. Immunoblotting

Both fractions of each tissue were applied to SDS-PAGE, transferred onto nitrocellulose membrane, probed with a rabbit polyclonal antibody against GFP (MBL, Nagoya, Japan), PLAP (Biomeda), TESP5, PH-20, acrosin or mouse monoclonal antibody against fertilin-β, and detected using the ECL-system (Amersham Bioscience).

1.4. PLAP Conversion Assay

This assay uses a nature of nonionic detergent, TritonX-114, which distributes water-soluble molecules and hydrophobia molecules soluble to detergent. By the PLAP conversion assay, GPI-anchored protein releasing activity in a course of purification was monitored. PLAP was prepared by expressing cDNA in COS7 cells, extracted by buffer containing 20 mM Tris, pH 8.0, 150 mM NaCl, 1% TritonX-114, Complete™ protease-inhibitor and the detergent-soluble phase was collected after partitioning at 37° C. PLAP was purified by DEAE-cellulose ionic exchange liquid chromatography (LC) (elution buffer: 20 nM tris pH8.0, 0.1% TritonX-100, 0 mM-500 mM NaCl gradient) and anti-PLAP antibody column (antibody: rabbit anti-PLAP polyclonal antibody, Biomeda; Column: Hitrap NHS-Activated HP, Amercham Bioscience; elution buffer: 100 mM glycine pH2.8). Using detergent-soluble PLAP protein as substrate performed assay. PLAP activity was measured with an alkaline phosphatase detection kit (Nacalai tesque). The conversion reaction was performed in 100 mM Tris, pH 7.5, 5 mM $CaCl_2$, 150 mM NaCl and 0.3 IU/ml of PLAP for 90 min at 37° C. The reaction was stopped by adding TritonX-114 at a final concentration of 2% and 1 mM EDTA, followed by microcentrifugation at 25° C. The water-soluble phase was collected and PLAP activity was measured by the alkaline phosphatase detection kit. The water-soluble phase was also applied to immunoblotting using anit-PLAP polyclonal antibody (Biomeda, Foster City, USA).

1.5. Purification of GPI-Anchored Protein Releasing Substance

Germ cells prepared from 500 testes of adult ICR mice were cut in a size of less than 1 mm$^3$ using razor. Isolation of germ cells was performed repetitive suctioning with pipette. After removing vas deferens by light centrifugation, supernatant was recovered and further precipitated by centrifuging at 1500×g. The precipitate was crushed and sonificaterd in a buffer containing 3 mM Tris pH 7.4, 2 mM $MgCl_2$, 1 mM EDTA, 0.25 M sucrose, and Complete™ protease-inhibitor, and homogenates were centrifuged at 100,000×g for 1 hour. The pellet was solubilized in a buffer containing 20 mM Tris, pH 8.0, 1% TritonX-100, and Complete™ protease-inhibitor, Lysates were ultracentrifuged (100,000×g) for 1 hour, and the supernatant was collected. This sample was applied to serial LCs.
1) DEAE-cellulose (Seikagaku); elution with a buffer containing 20 mM Tris pH8.0, 0.1% TritonX-100, 0 mM-500 mM NaCl gradient.
2) Phenyl-Sepharose CL-4B (Amersham Bioscience); elution with a buffer containing 20 mM Tris pH7.5, 0.1% TritonX-100.
3) ConA-Sepharose 4B (Amersham Bioscience); elution with a buffer containing 20 mM tris pH7.5, 0.1% TritonX-100, 150 mM NaCl, 500 mM methyl-α-monnopyranosid (Seikagakukougyo, Tokyo).
4) TSK gel 3000SW (Tosoh): elution with a buffer containing 20 mM tris pH7.5, 0.1% TritonX-100, 150 mM NaCl.

1.6. Proteomics Analysis

Purified peptides were separated by SDS-PAGE, digested with a 70% formalin solution containing trypsin or 0.1 M cyanogen bromide, and then we applied to the capillary HPLC (Magic, Michrom) and ion-trap mass spectrometry (ThermoFinnigan). Sequest and Mascot search were done for each obtained signal. Peptides labeled with S mass spectrum were separated with trypsin-digested reverse HPLC, and identified with automatic peptide sequencer.

1.7. Cell Culture and Transfection

F9, HeLa and COS7 cells were cultured in DMEM supplemented with 10% FCS. For DNA transfection, lipofectamine reagents (Life Technologies, Rockville, USA) were used according to the manufacturer's protocol.

1.8. ACE Samples

ACE cDNA was obtained by reverse transcription-polymerase chain reaction (RT-PCR) using mouse testis cDNA as a template and primer pairs:

```
5'-tgaattccaccatgggccaaggttgggctactc    (SEQ ID NO:
                                         1)
cagg-3';
and 5'-gaattcgtcacttatcatcatcatccttataat    (SEQ ID NO.
                                         2)
cctgctgtggctccaggtacaggc-3'.
```

The obtained PCR product encodes a FLAG-tagged version of the soluble testicular isoform. The cDNA for peptidase-inactivated mutant with amino acid Glu414 replaced by Asp was prepared by the site-directed mutagenesis with the mutation promer:

5'-cttggtgatag cgcaccacga tatgggccac atccagtatt tcatgca-3' (SEQ ID NO: 3).

The culture supernatants of COS7 cells transfected with the ACE cDNAs were collected and recombinant ACEs were purified by anti-FLAG M2-agarose affinity column (Sigma). The somatic isoform of ACE (ACE-S) from rabbit lung (Sigma A-6778) was also used according to the manufacturer's protocol. The peptidase activity of the ACE was measured by the reported method (Kawahara and Ashihara, Clin. Chem. 27:1922-1925, 1981).

1.9. FACS Analysis

Cells were detached from plate with 0.02% EDTA-PBS, and immersed in Hank's adjusted salt solution containing 1% BSA. Suspended cells were treated with 10 μg/ml filipin/PBS (Sigma) for 1 h. at 0° C. Cells were then treated with ACE, 1.0 IU/ml of PI-PLC (GLYKO) or PBS alone for 1 h at 37° C. under the condition of presence or absence of captopril (Sigma). After the cells were repeatedly immersed into 1% BSA, the cells were stained with biotin-conjugated antibodies for human CD59, human DAF, mouse Sca-1 (Pharmingen-Fujisawa), mouse Thy1.2 (Pharmingen-Fujisawa), mouse E-cadherin (Takarasyuzo), or human prion protein (3F4, Signet Laboratories), then treated with phycoerythrin-conjugated streptavidin (Pharmingen-Fujisawa). For testing the prion protein-releasing activity, human embryo fibroblasts were stained with the monoclonal antibody for human prion protein, 3F4 (Signet Laboratories). The stained cells were applied to a FACScan cell sorter. Survivability of the sorted cells was evaluated with FSC and SSC channels. EGFP-GPI expressed in F9 cells was directly detected. For quantification of shedding, the percent shedding value was calculated from the mean fluorescence values for each cell population:

$$(\%) \text{ Shedding} = \frac{\text{ACE}(?)-\text{ACE}(+)}{\text{ACE}(?) - PI\text{-}PLC} \times 100$$

The mean fluorescence value of PI-PLC-treated population was defined as the maximum shedding and that of ACE(?) as no shedding.

1.10. Radiolabeling Analysis

F9 cells expressing EGFP-GPI were metabolically labeled with 0.2 mCi/ml of [$^{32}$P]-orthophosphoric acid (Amersham Bioscience) or 0.1 mCi/ml of [$^{3}$H]-ethanolamine (Amersham Bioscience) for 16 h. Filipin-pretreated cells were incubated with 0.5 μM of ACE, 1.0 IU/ml of PI-PLC or 10% lysate of mouse submaxillary gland containing mouse glandular kallikrein (mGK; enzyme digesting EGFP at near C-terminus) for 1 h at 37° C. Released EGFP was immunoprecipitated with anti-GFP antibody, subjected to SDS-PAGE and transferred onto nitrocellulose membrane. The quantity of EGFP-GPI protein was evaluated by measuring the density of bands detected on EGFP immunoblotting by using a densitometer (Molecular Device) and radioactivity of the cognate band was determined by a liquid scintillation counter.

1.11. Sperm-Egg Binding Assay

All gametes were placed and handled within TYH medium. Parochis were isolated from wild-type mice and ACE knockout mice, and dispersed in 250 μl of medium. After sperms were floated for 15 minutes, transferred to 1.5 ml medium and incubated for at least 1 hour. Eggs were separated from superovulated mice and treated with 1 mg/ml of hyaluronidase (Sigma) on THY medium for removing laminated cells. Incubated sperms (approximately 2.0×10$^6$ sperm/ml) were treated for 90 min with 0.2 U wild-type ACE (ACE-WT), 0.2 U ACE-E414D, 1.0 IU/ml PI-PLC, or 1.0 ml PI-PLC with 4 mM inositol monophosphate (Sigma), 4 mM inositol monophosphate, and buffer (PBS) alone. For the sperm-egg (zona pellucida) binding assay, gametes were co-incubated in a TYH droplet covered with mineral oil for 1 h, washed gently in PBS and fixed with 4% paraformaldehyde/PBS. The oocytes were visualized at 200× under a light microscope (Olympus) and the number of sperms was counted at a focus showing the widest diameter of eggs.

2. Results and Discussions 2.1. Property of EGFP-GPI in Transgenic Mouse Lines

FIG. 1 shows EGFP-GPI fluorescence of testis in EGFP-GPI transgenic mouse lines. Expression of EGFP-GPI in germ cells (Gc) was found in the line 2 testis but not in lines 1 and 3.

Figure 2:
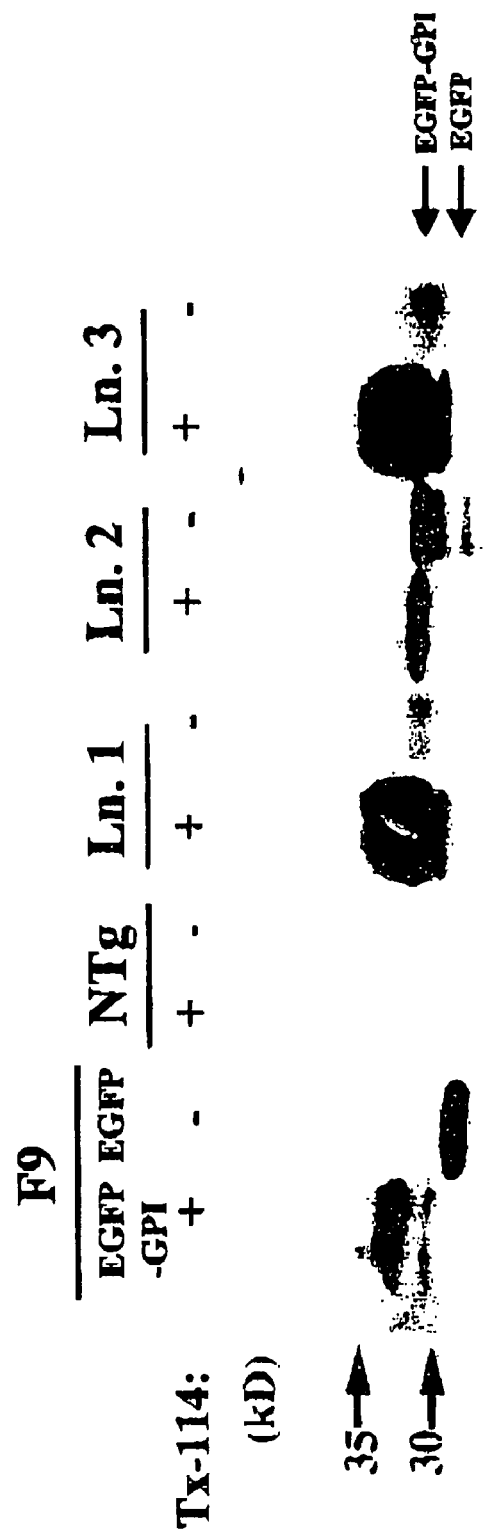
FIG. 2 shows physicochemical property of EGFP-GPI in the testis of EGFP-GPI transgenic mouse analyzed by gel electrophoresis. Tissues were led to dissolve in the buffer with (Tx-114+) or without (Tx-114−) detergent and amounts of lysate were applied to immunoblotting. EGFP-GPI could be dissolved by detergent-less buffer solely in the line 2 testis. It should be noted that the size of water-soluble protein (Ln. 2 Tx-114−) was similar with that of membrane-bound protein (Ln. 2, Tx-114+). F9, F9 cells transfected with EGFP-GPI. Ntg, non-transgenic control.

FIG. 2 shows solubility of EGFP-GPI in transgenic testes. Tissues were solubilized with buffer containing detergent (Tx-114+) or buffer without detergent (Tx-114−) and a part of the solubilized matter were subjected to western blotting. EGFP-GPI was led to solubilized with Tx-114− buffer solely in line 2 testis. It is notable that size of water-soluble protein (Ln. 2, Tx-114−) was equivalent to membrane-anchored one (Ln. 2, Tx-114+).

2.2. Identification of GPI-Anchored Protein Releasing Factor.

Figure 3:
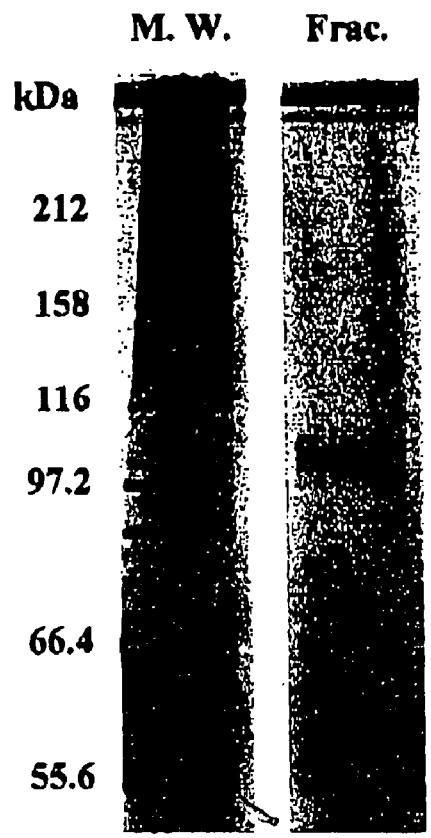
FIG. 3 is a molecule showing GPI-anchored protein releasing activity that is purified from continuous liquid chromatography. It was isolated as a single 100-kDa band with SDS-PAGE and silver staining from a peak fraction eluted from TSK gel 3000SW column.

Identification of GPI-anchored protein releasing factor was intended by using EGFP-GPI transgenic mice, and the targeted 100 kDa protein was purified. The membrane-rich fraction of germ cells from mouse testis was solubilized in a buffer containing 1% Triton X-100, centrifuged and the supernatant was collected and subjected to chromatographic fractionation. The PLAP conversion assay was performed on the eluted fractions and the maximum values are shown in Table 1. All reactions were performed using PI-PLC (1.0 IU/ml), the value of which was defined as maximum reaction. FIG. 3 shows a single 100 kDa band detected by silver staining.

TABLE 1

| Column | Volume (ml) | Total protein (mg) | Total activity (U)* | Specific activity (U/mg protein) | Fold purification |
|---|---|---|---|---|---|
| S-100 sup. | 393 | 19100 | 336160 | 18 | 1.0 |
| DEAE-cellulose | 8 | 228 | 14410 | 63 | 3.5 |
| Phenyl-sepharose | 8 | 212 | 17596 | 83 | 4.6 |
| Con-A-sepharose | 1 | 6 | 6100 | 1017 | 56.5 |
| TSK gel 3000SW | 1 | 1 | 2500 | 2500 | 138.9 |

$$*U\,(Unit\,X) = \frac{sample - background}{PI\text{-}PLC - background}$$

Figure 4:
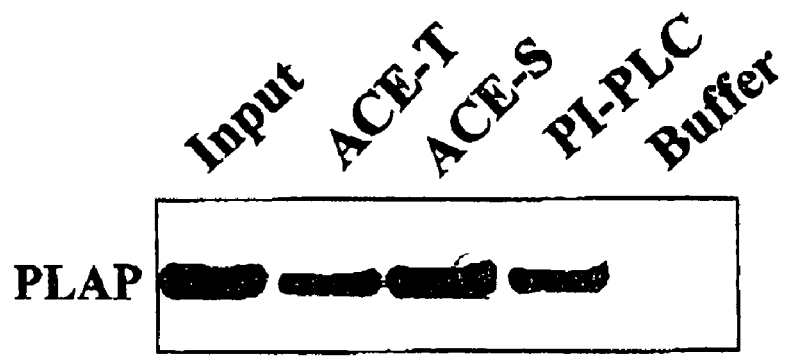
FIG. 4 is immunoblotting of released PLAP from reaction with purified recombinant ACE (ACE-T), purchased ACE-S, PI-PLC or Buffer alone. Input indicates substrate of the reaction.

This protein was subsequently identified as ACE by proteomics analysis. Then, the activity of the purified protein was compared with that of a recombinant ACE and a commercially available ACE. That is, to confirm whether the recombinant ACE and a commercially available ACE could change the PLAP to be soluble, a partially purified PLAP was reacted with a recombinant ACE (ACE-T) or a commercially available ACE (ACE-S). After treating with TritonX-114, a part of soluble phase was applied to SDS-PAGE and detected by immunoblotting. The results were shown in FIG. 4. Though the band corresponding to the soluble PLAP was slightly small compared with the sample treated with the PI-PLC, it was detected in both sample with ACE-T and ACE-S.

Figure 5:
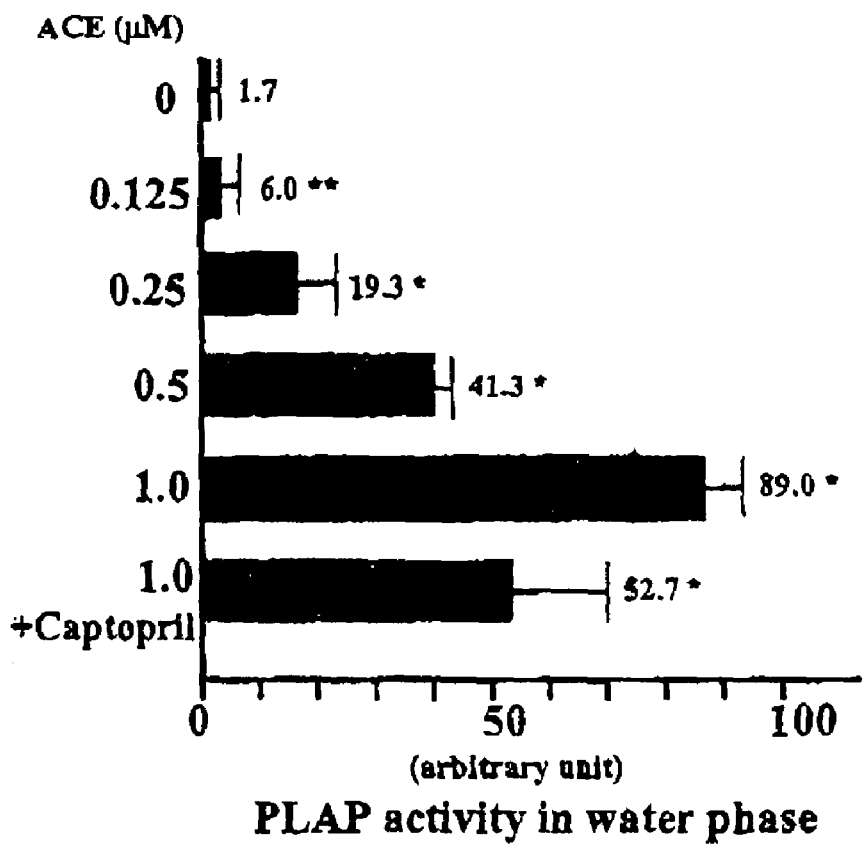
FIG. 5 shows a result of measurement for dose-dependence of ACE reaction. The partially purified PLAP was reacted with various concentration of ACE-S and PLAP activity in aqueous phase was measured. Values are mean±SD, n=3.0 mU/ml for Control. Student's t-test, *: $p<0.01$, **: $p<0.05$. The lowest bar shows the reaction when $10^{-3}$ M captopril was added.

A dose-dependent activity of ACE was assessed by reacting the partially purified PLAP with ACE-S of various concentrations and measuring soluble PLAP activity. The results were shown in FIG. 5. The ACE activity was dose-dependent manner in the commercial ACEs, and it was inhibited with the specific ACE inhibitor, captopril.

Figure 6:
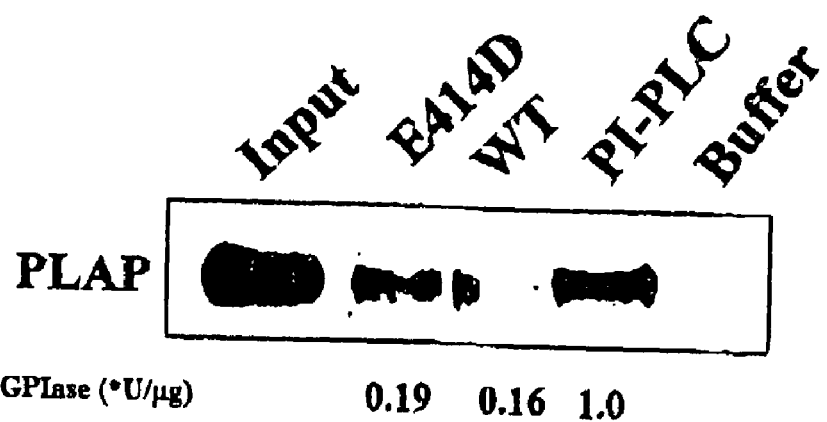
FIG. 6 is a GPI-anchored protein releasing activity measured by immunoblotting of PLAP reacted with ACE. The E414D is a mutant that Glu414 in the peptidase active site was substituted to Asp. WT, wild-type ACE-T; Buffer, vehicle alone. The unit was defined and calculated as in Table 1. Input indicates substrate of the reaction.
Figure 7:
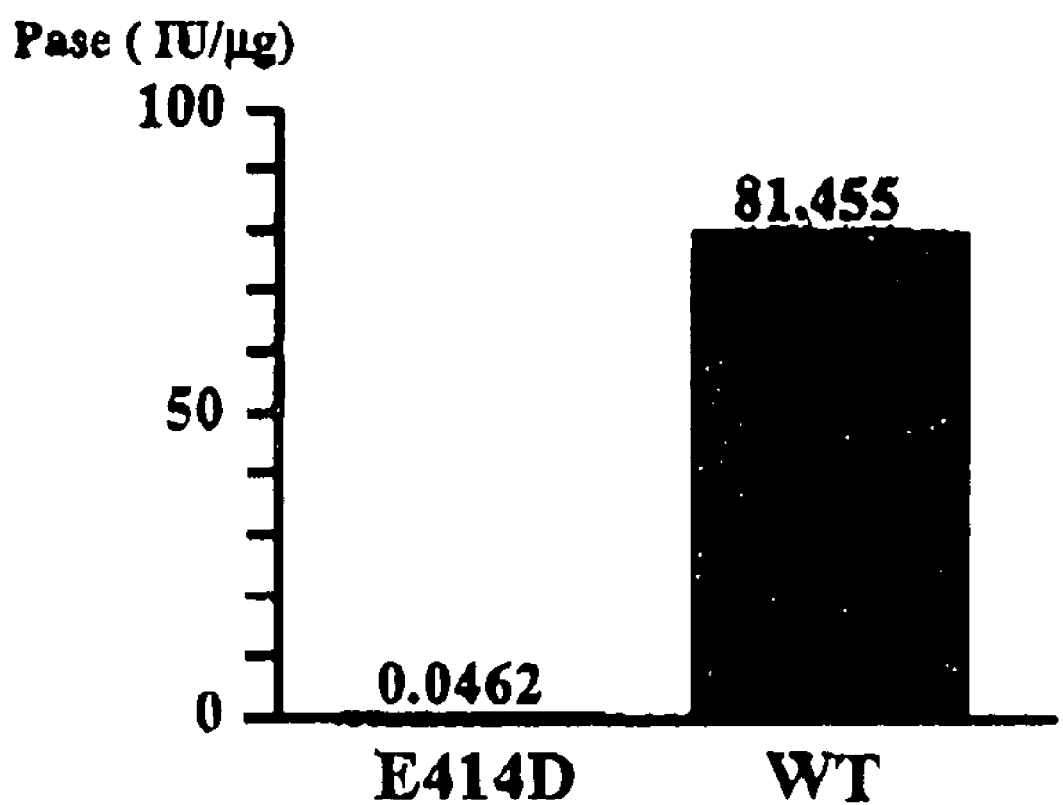
FIG. 7 is a measurement of peptidase activity (Pase). The E414D is a mutant that Glu414 in the peptidase active site was substituted to Asp. WT, wild-type ACE-T. Procedures were accorded with the description of Kasahara and Ashihara, Clin Chem. 27:1922-1925.

Since the Glu414 of ACE has been known as essential for peptidase activity, a recombinant ACE (E414D), of which Glu414 was replaced with Asp, was prepared and GPI-anchored protein releasing activity and peptidase activity thereof were measured (FIGS. 6 and 7). Compared with wild-type ACE, peptidase activity of ACE (E414D) was decreased to less than 1/1000, while the GPI-anchored protein releasing activity was not changed. These results suggest that the active site element for the GPI-anchored protein releasing activity differ from that for peptidase activity.

2-3. Effect of ACE to GPI-Anchored Proteins

Figure 8:
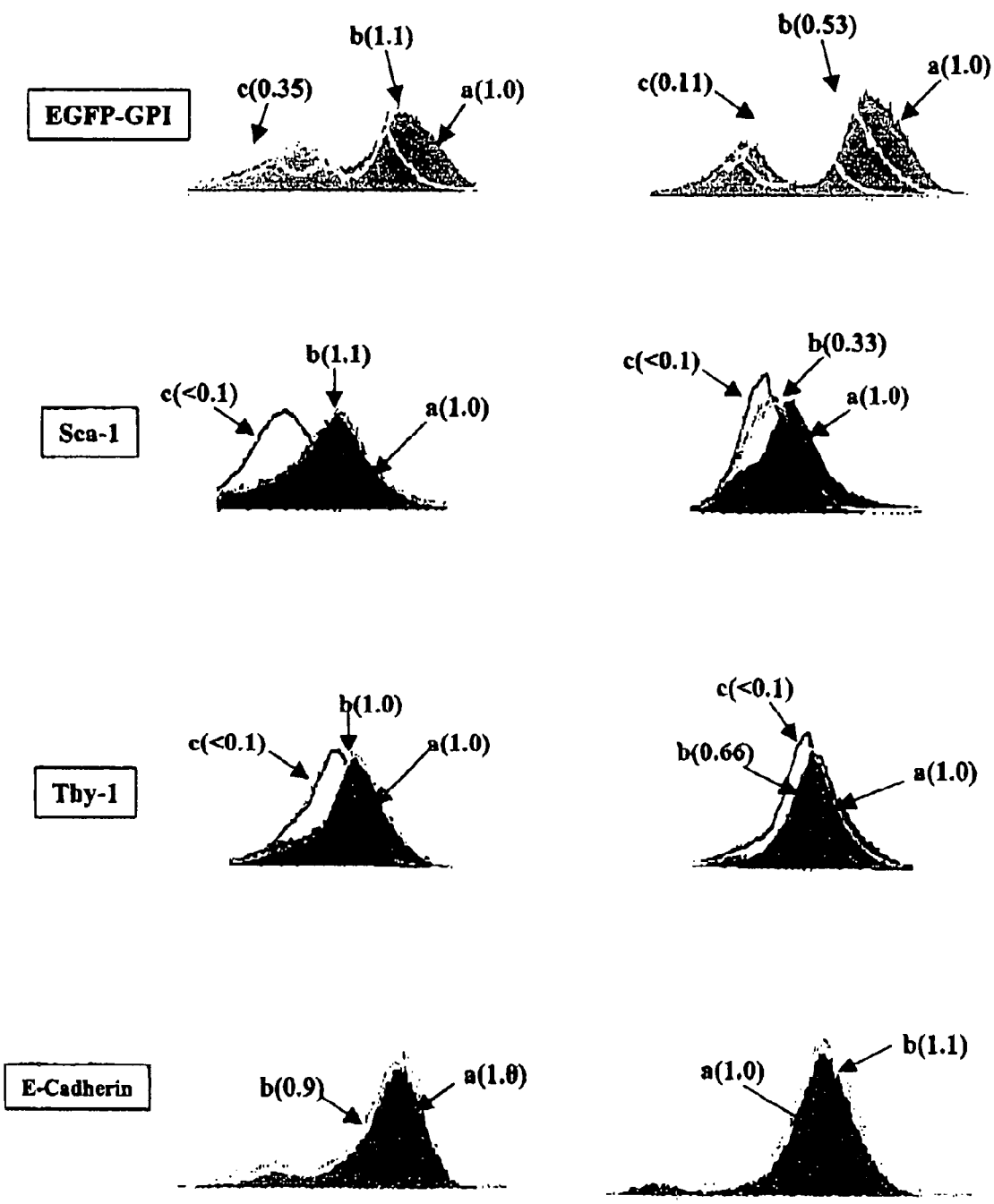
FIG. 8 shows the result of FACS analysis. The F9 cells to which EGFP-GPI was transfected, were reacted with 1.0 U/ml of ACE-S under the condition of pre-treatment of filipin (right) or non-treatment of filipin (left). Expressions of EGFP-GPI, Sca-1, Thy-1 and E-cadherin from the cell surface were analyzed. Expressions of the GPI-anchored proteins were declined after filipin treatment (left-side sift of cell number), but not the transmembrane protein E-cadherin. The degree of shedding was different among proteins (% shedding: EGFP-GPI, 53%; Sca-1, 67%; Thy-1, 34%). a, ACE(−); b, ACE(+); c, PI-PLC. Numbers for each line are mean values.
Figure 9:
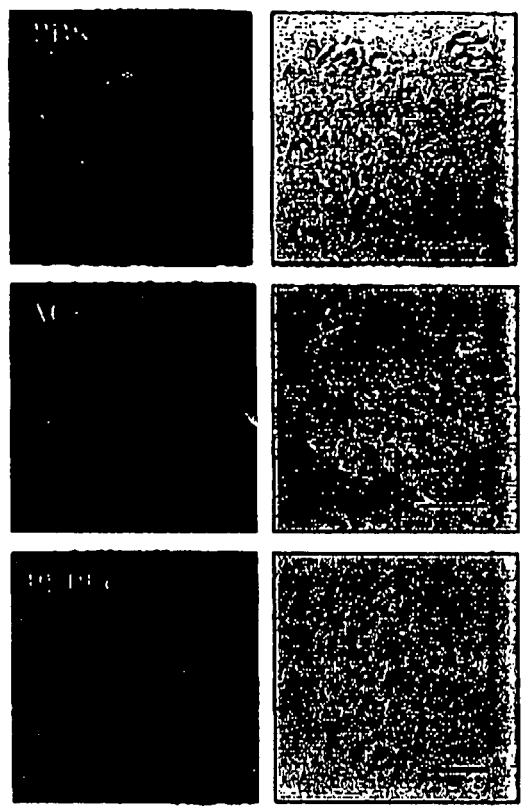
FIG. 9 shows GFP fluorescence on EGFP-GPI expressing F9 cells after ACE or PI-PLC treatment examined by fluorescence microscopy. Note that ACE cleaves out EGFP-GPI from cell surface and the fluorescence of Golgi complex remained the same. Magnification, 200×. PBS, control without ACE and PI-PLCX treatment.

Effect of ACE to GPI-anchored proteins was examined by using the F9 cell clone, which stably expressed EGFP-GPI on the cell surface. The F9 cells were reacted with 1.0 U/ml of ACE-S or 2.8 U/ml of PI-PLC under the condition of pre-treatment of filipin or non-treatment of filipin. Dynamics of EGFP-GPI was analyzed with GFP fluorescence observation and cell surface expressions of EGFP-GPI, Sca-1, Thy-1 and E-cadherin were with FACS analyiss. Although ACE exhibited little effect on EGFP-GPI expression, pre-treatment of cells with filipin allowed ACE to shed EGFP-GPI from the cell surface (FIGS. 8 and 9). Most of the GPI-anchored proteins are localized and packed in the lipid raft, suggesting that exogenous ACE is prevented from accessing the substrate molecules by this membrane microstructure. It was also confirmed that other GPI-anchored proteins, Sca-1 and Thy-1 were similarly released by ACE treatment of cells. In contrast, both ACE and PT-PLC had no effect on the transmembrane protein E-cadherin, implying that the activity of ACE is unique for GPI-anchored protein shedding.

Figure 10:
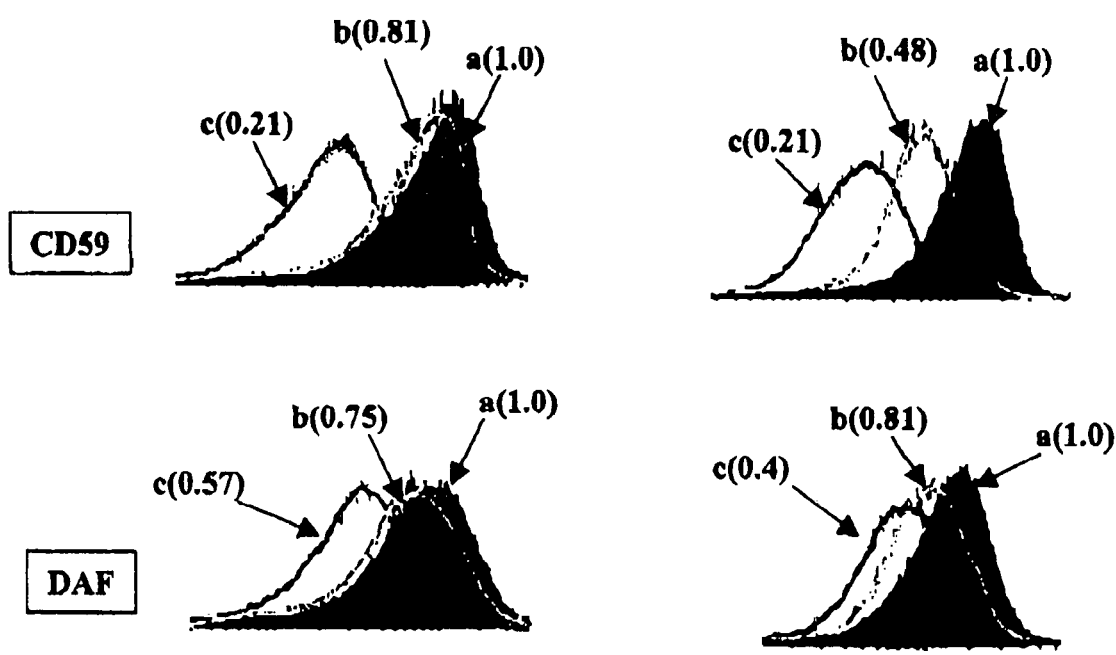
FIG. 10 shows the result of FACS analysis. HeLa cells were reacted with 1.0 U/ml of ACE-E or 2.8 U/ml of PI-PLC under the condition of pre-treatment of filipin (right) or non-treatment of filipin (left). Expressions of CD59 and DAF from the cell surface were analyzed. Expressions of the proteins were declined with ACE treatment (left-side sift of cell number). The degree of shedding was 66% for CD59 and 58% for DAF with filipin pre-treatment.
Figure 11:
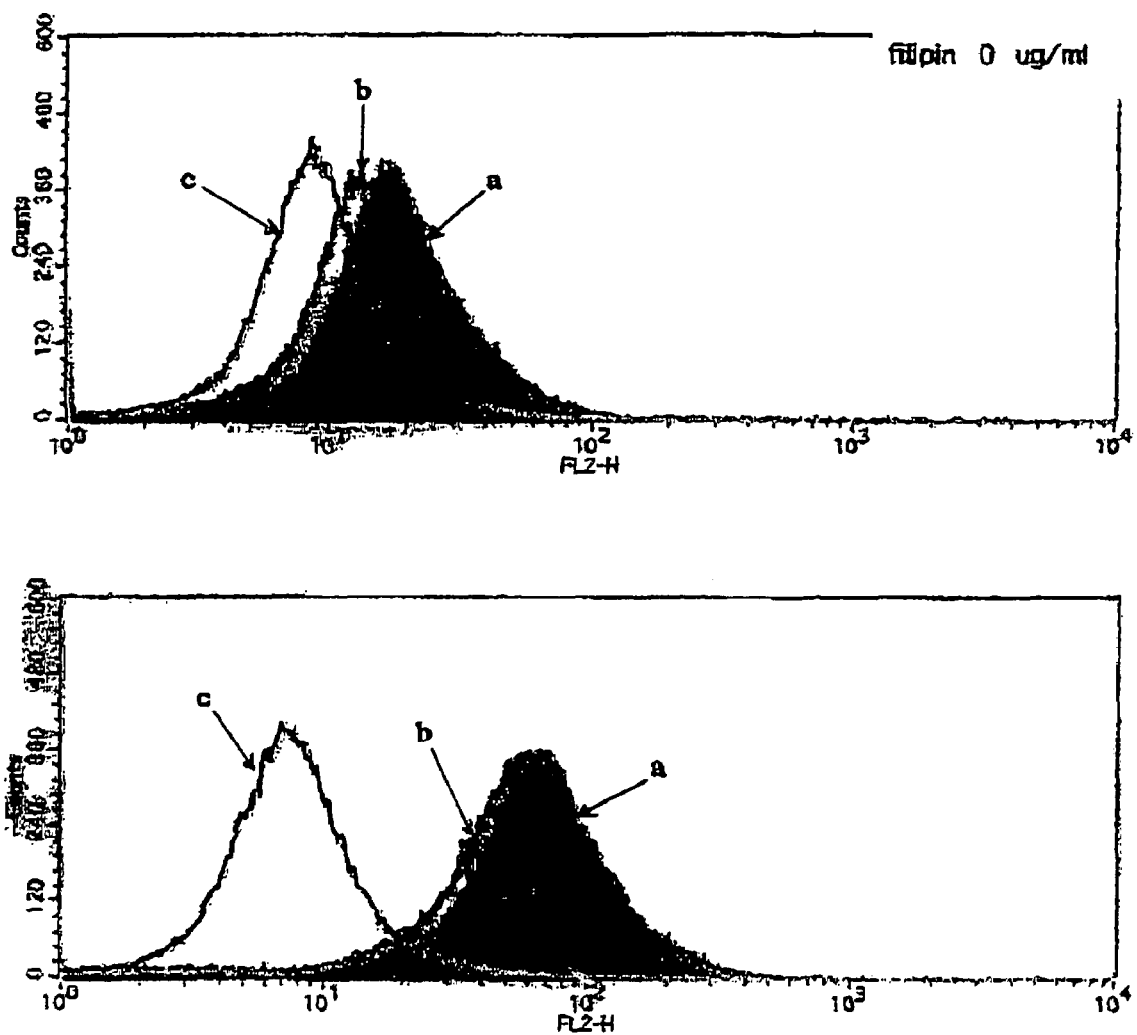
FIG. 11 shows the result of FACS analysis in which shedding of prion protein from HEK293 cell by treatment of ACE-S (1.0 U/ml) was measured. Lower panel shows shedding of CD59 as a control.
Figure 12:
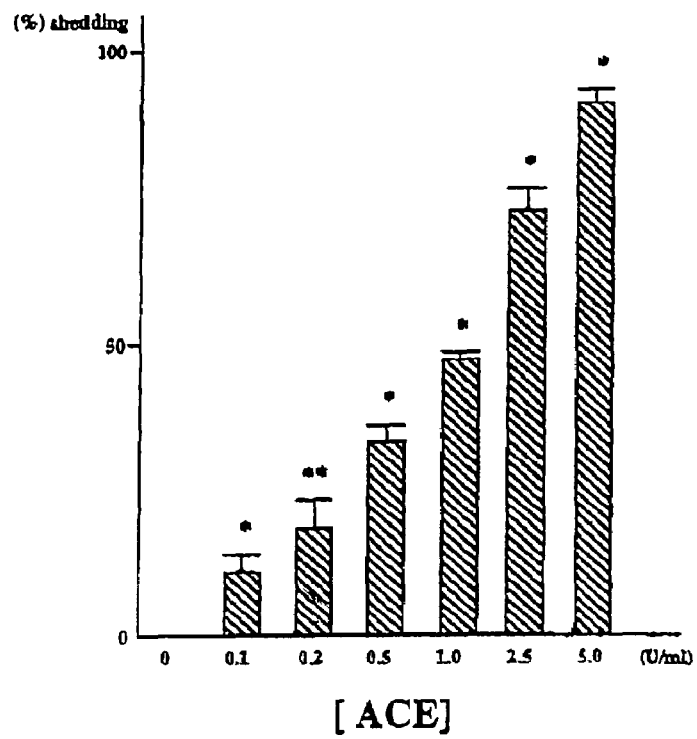
FIG. 12 shows the result of FACS analysis, in which expression of CD59 by various concentrations of ACE-S in filipin pre-treated HeLa cell was measured and shedding % was calculated. Values are mean±SD, n=3. 0 U/ml for control. Student's t-test, *: $p<0.005$, **: $p<0.01$.
Figure 13:
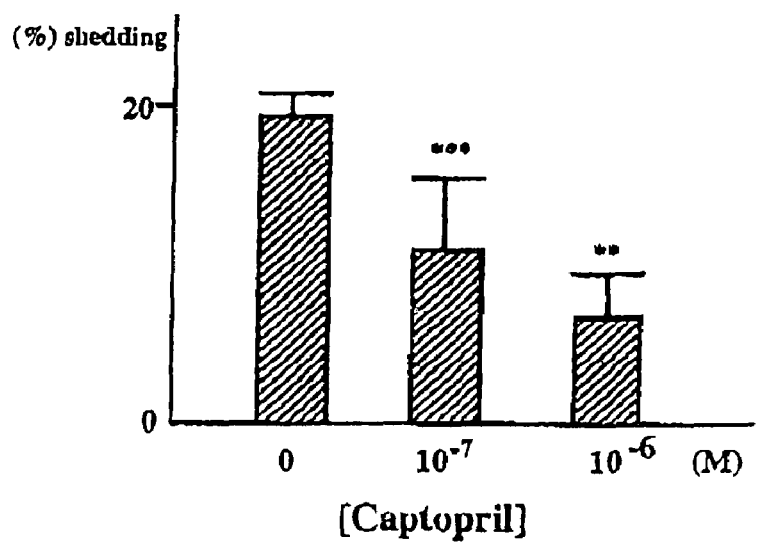
FIG. 13 shows the result of FACS analysis. The filipin pre-treated HeLa cells were incubated with 0.2 U/ml of ACE-S corresponding to $10^{-7}$ M ACE peptide under the presence of indicated amount of captopril. Values are mean±SD, n=3. Control is the case of 0 M captpril. Student's t-test, *: $p<0.01$, **: $p<0.05$.
Figure 14:
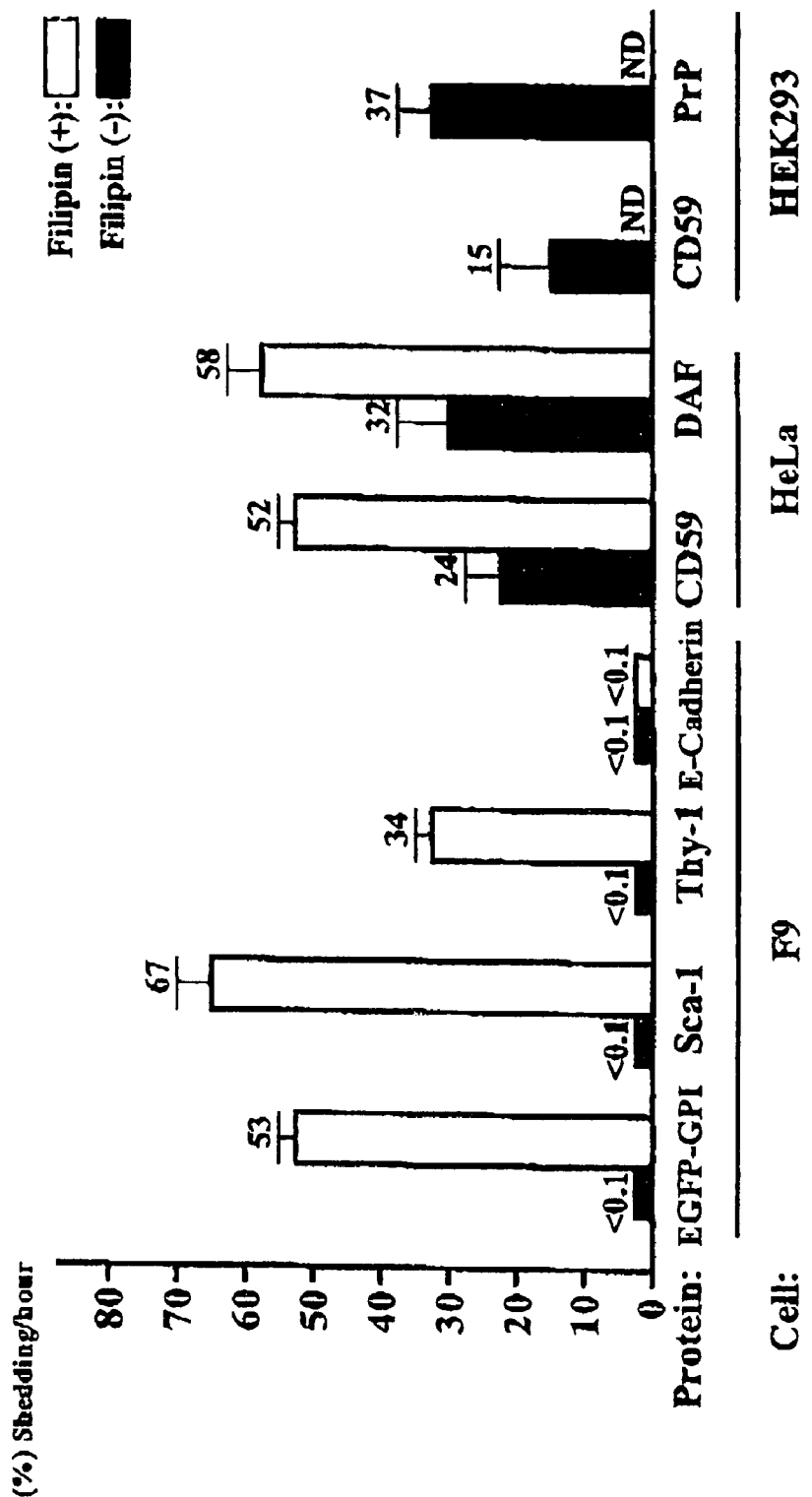
FIG. 14 is a comparison of shedding activity of ACE for various proteins, and a summary of FIG. 8, FIG. 10 and FIG. 11. ACE caused shedding of various endogenous GPI-anchored proteins, except transmembrane protein E-cadherin. That is, EGFP-GPI, Sca-1, Thy-1 and E-cadherin in F9 cells expressing EGFP-GPI; CD59 and the decay-accelerating factor (DAF) in HeLa cells; and prion protein (PrP) and CD59 in HEK293 cells were subjected to FACS analysis. Values are mean±SD, n=3. ND, not determined.

The effect of ACE activity was further examined for CD59 and the decay-accelerating factor (DAF) in HeLa cells; and prion protein in HEK293 cells by using FACS analysis (FIGS. 10 and 11). As a result, it was confirmed that all proteins were efficiently shed from cell surface. ACE shedding activity for CD59 in HeLa cells was more clearly in the case of disrupting lipid raft by treatment of cholesterol blocking agent, filipin (FIG. 10), which effect was ACE dose-dependent (FIG. 12) and was inhibited by captopril (FIG. 13). In contrast to F9 cell molecules, GPI-anchored proteins on human cells were readily released from the cell surface without filipin treatment (FIG. 14).

2.4. Identification of Cleavage Site of ACE on Substrates

F9 cells expressing both EGFP-GPI were treated with ACE and PLAP, and released products were purified by antibody-conjugated columns. Attempts to identify the structure of the carboxy-terminal peptides several times by HPLC/mass spectrometry with trypsin, cyanogen bromide or *Staphylococcus aureus* V8 protease treatments of both proteins failed to recover the target peptides. It is assumed from this result that the released GFP-GPI has GPI-anchor components at its C-terminus.

Figure 15:
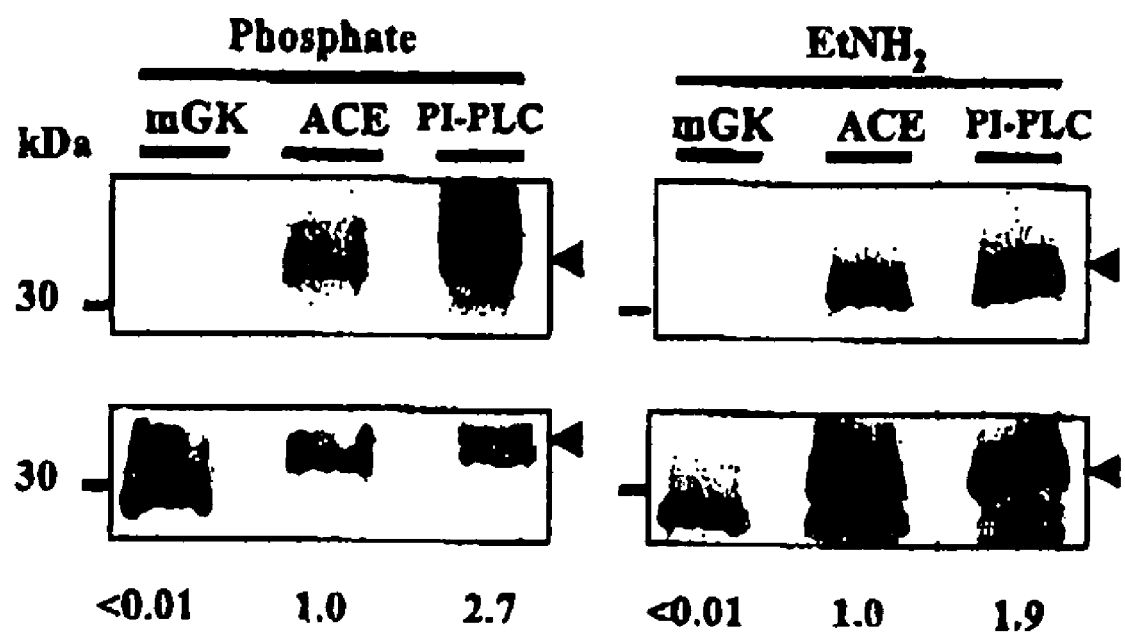
FIG. 15 is detection of GPI-anchor moiety in thy released products. The F9 cells expressing EGFP-GPI were metabolically labeled with $^{32}$P phosphate or $^{3}$H ethanolamine, and were treated with filipin. Then cells were treated with ACE, PI-PLC or mouse glandular kallikrein (mgk). The released EGFP-GPI proteins were trapped using anti-GFP antibody, applied to SDS-PAGE and transferred onto nitrocellulose membrane. The total amount of the released EGFP-GPI proteins was detected from the intensity of bands from EGFP immunoblotting. With radiological analysis, the same bands were detected at the arrowed portion. The radioactivity per quantity of protein was calculated and indicated as a relative value to the amount of ACE-treated sample considered 1.0. Rapid migrating bands detected in the ACE-treated sample should be due to digestion by any enzyme present in F9 cells.

Therefore, the F9 cells expressing EGFP-GPI were metabolically labeled with [$^{32}$P]-phosphate or [$^{3}$H]-ethanolamine, and treated with ACE, PI-PLC or mGK. Then, the released proteins from the cells were applied to EGFP immunoblotting, to measure radioactivity for each band (FIG. 15). Measurements were performed at least four times, and the almost same results were obtained. Although the released EGFP-GPI products with $^{32}$P or $^{3}$H labeling were not detected by mGK treatments, both were detected by ACE treatment or PI-PLC treatment, indicating the presence of a portion of GPI-anchor structure in the ACE-released molecules. Further, the radioactivities of released-products were found to be about one-third when it was labeled on the phosphate and a half on the ethanolamine compared with those of PI-PLC-released molecules. As shown on FIG. 16, radioactive isotopes for labels were localized on GPI anchors, and it was suggested from the difference of radioactivity that the ACE cleavage site is nearer to the GPI-anchored proteins than that of PI-PLC, and more precisely that the cleavage site might be near the three-consecutive mannoses of GPI anchor bone to which the anchor proteins bind.

2.5. Effect of ACE on the Sperm Lacking Egg-Binding Activity

The most prominent phenotype of ACE knockout mouse is male infertility. Compared with wild-type sperms, ACE knockout sperms showed defective sperm-egg binding at the zona pellucida (Krege et al., Nature 375: 146-148,1995).

Figure 17:
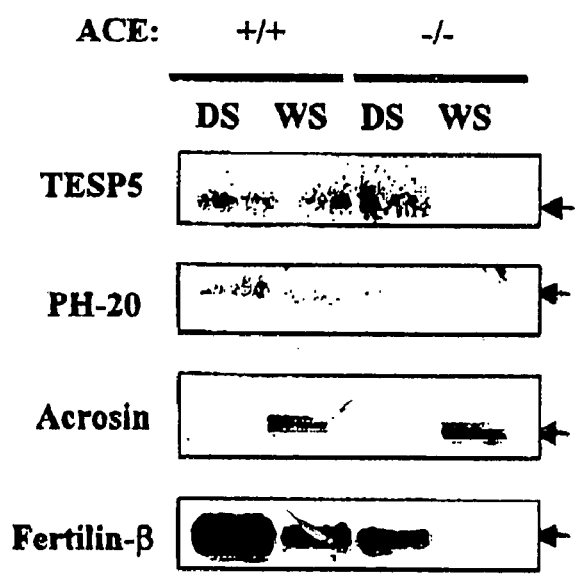
FIG. 17 shows the immunoblotting of the proteins in the sperm of wild-type and ACE knockout mice. Epididymal sperms from both wild-type and knockout mice were collected and distributed into water-soluble fraction (WS) such as acrosome and detergent-soluble fraction (DS) such as cell membrane component proteins, which were then separated using SDS-PAGE and blotted with antibodies. Aerosin and fertilin-β in sperm X were used as target proteins for WS and DS, respectively. Uncertainly, expression of fertilin-β in ACE knockout mice was lower than of wild-type mice. +/+, wild-type; −/−, ACE knockout.

Epididymal sperms were collected from both wild-type and knockout mice and distributed into water-soluble fraction (WS) and detergent-soluble (DS) fraction. Then, GPI-anchored proteins, Tesp5 and Ph-20, which are known to be released from the sperm during fertilization (Non-patent Documents 3 and 4), in the fractions were analyzed with immunoblotting (FIG. 17). Since aqueous proteins released from sperm are distributed in soluble traction, both Tesp5 and Ph-20 were detected from water-soluble fraction (WS) of wild-type sperm but not in the knockout sperm, implying that ACE is essential for release of GPI-anchored proteins.

Figure 18:
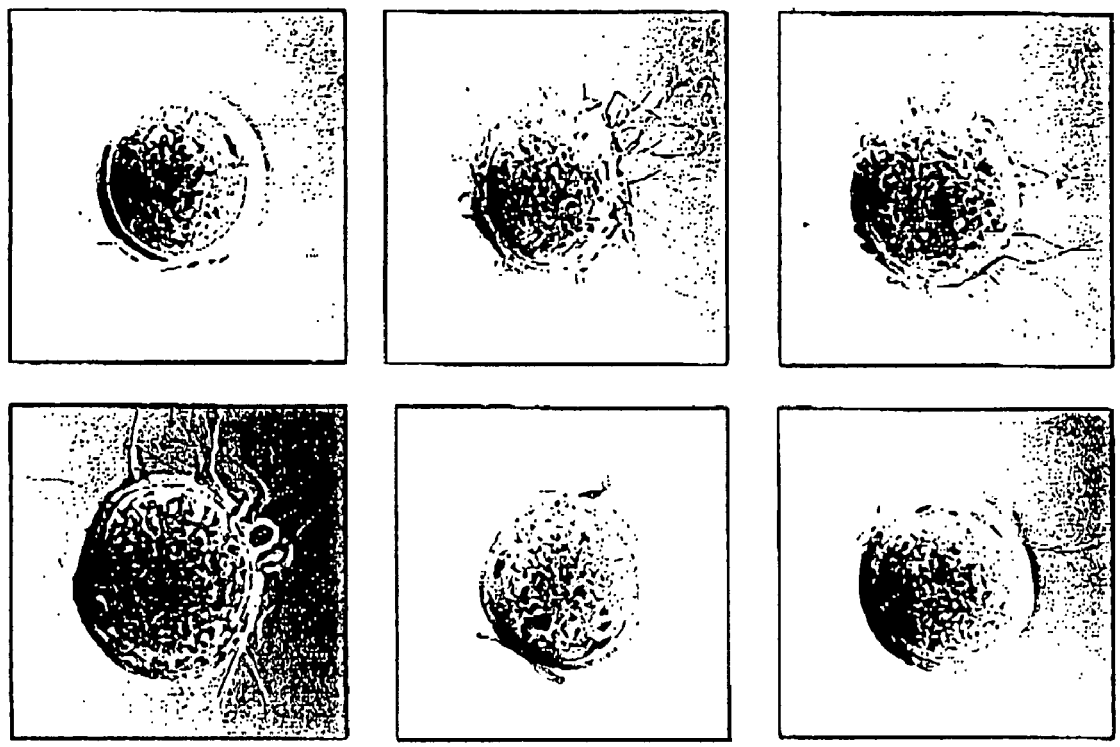
FIG. 18 is microscopic image showing binding or ACE knockout sperm to the zona pellucida after various treatments, Magnification is 200×. Substances for the pre-treatment were indicated in the image. ACE-WT, wild-type ACE; ACE-E414D, peptidase-inactivated ACE mutant; Inositol-P, a PI-PLC-specific inhibitor; Buffer, control using buffer for the pre-treatment.
Figure 19:
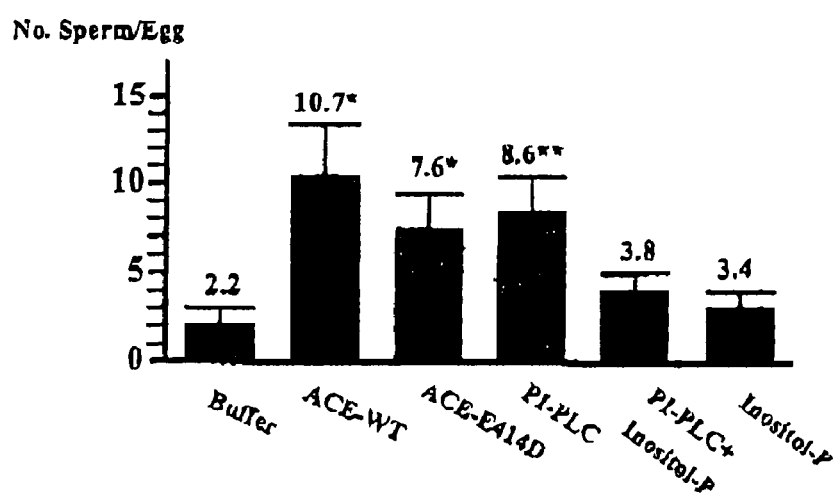
FIG. 19 is a graph summarizing sperm number bound to the egg in FIG. 18. Values are mean±SEM. Numbers of eggs were 18 or Buffer, 20 for ACE-WT, 17 for ACE-E414D, 18 for PI-PLC, 18 for PI-PLC+Inositol-P and 17 for Inositol-P. Student's t-test, *$p<0.001$, **$p<0.005$; compared with Buffer control; $p<0.3$, comparison of ACE-WT with ACE-E414D; $p<0.5$, comparison of ACE-WT with PI-PLC; $p<0.05$, comparison of PI-PLC with PI-PLC+Inositol-P.

In addition, the effect of ACE on sperm-egg binding was examined. That is, Epididymal sperms of both wild-type and knockout mice were treated with either wild-type or peptidase-inactivated (E414D) ACEs or PI-PLC and then incubated with unfertilized eggs from C57BL/6 mice. These treatments had no effects on wild-type sperm-zona binding. In contrast, treatment with wild-type or peptidase-inactivated ACE vigorously restored sperm-zona binding defect of the ACE knockout mice (FIGS. 18 and 19). Moreover, PI-PLC treatment apparently cured the egg binding ability of ACE knockout sperms to a level comparable with both ACE treatments, confirmed by inhibition with inositol monophosphate, a PI-PLC-specific inhibitor. These results indicate that GPIase activity of ACE is crucial for sperm ability to binding to eggs.

2.6. Character of ACE GPIase Activity and its Utility

As a protein showing GPI-anchor-cleaving activity (GPIase activity), GPI-PLD is only enzyme known so far in mammals. However, GPI-PLD has been reported to exhibits the GPIase activity only when it is expressed intracellularly in culture cells (Tujioka et al., Biochem. Biophys. Res. Commun. 251:737-747, 1998). Therefore, GPI-PLD has never been used as a medicine for the GPIase activity. In contrast, ACE has superior property that efficiently releases GPI-anchored protein by only adding to human cells or tissues without destroying cell membrane structure by any drug treatment.

Figure 16:
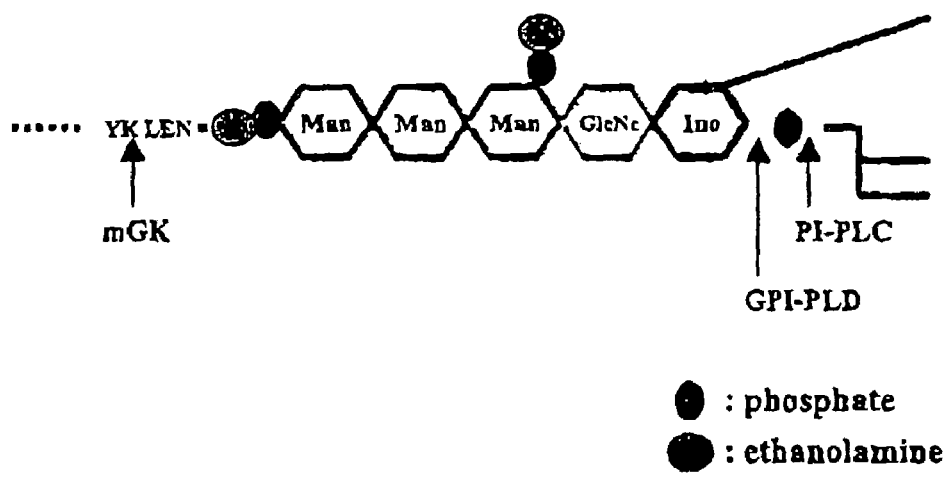
FIG. 16 is schematic representation of the GPI-anchor sugar chain backboen. Binding positions of phosphate and ethanolamine on the GPI-anchor backbone and also cleavage sites of PI-PLD, GPI-PLD and mGK were indicated. Man, mannose; GlcNc, glucosamine; Ino, inositol; black lines, lipid chains.

Another outstandingness of ACE is its cleaving site for the GPI-anchors, The cleaving site in the GPI-anchor structure as shown on FIG. 16, fatty acids addition to hydroxyl group of inositol (acylation) frequently occurs in matured GPI-anchors. As GPI-PLD cleaves site is just proximal to inositol (FIG. 16 and Hagaman et al., Proc. Natl. Acad. Sci. USA., 95: 2552-2557, 1998), it cannot X cleavage. Indeed, GPI-PLD could not release DAF from the intact erythrocyte having prominent acylation (Davitz et al., J. Biol. Chem., 264: 13760-13764, 1989). In contrast, shedding CD59 from the erythrocyte surface, ACE might cleave GPI-anchor possibly distal to the inositol moiety, with no influence on inositol acylation.

As another protein having GPIase activity, bacterial PI-PLC is also known. However, ACE is much safer than the PI-PLC in terms of usage of the GPIase activity for madicine, because it is an endogenous protein widely distributed in vivo.

ACE up-regulates blood pressure. Therefore, researches for developing ACE inhibiting drugs (antihypertension medication) or as to inhibition of peptidase activity have been made. The E414D mutant of ACE derived from rabbit ACE-S and mouse ACE-T that carries full GPIase activity but trace peptidase activity has clearly shown the prominent utility of ACE as GPIase drug.

INDUSTRIAL APPLICABILITY

As described above in detail, this invention provide a medicine for preventing or curing diseases, such as prion-related diseases, inflammatory diseases, bacterial infectious diseases and male infertility due to sperm-egg binding insufficiency, by releasing GPI-anchored proteins from the cell surface.

---

The invention claimed is:

1. A pharmaceutical composition for treating a disease by releasing glycosylphosphatidylinositol (GPI)-anchored protein from the cell surface, said composition comprising a mutant angiotensin-converting enzyme (ACE) consisting of the amino acid sequence of SEQ ID NO: 4 except Glu at position 414 is substituted with Asp; and a pharmaceutically acceptable carrier, wherein the disease is a prion-related disease, a bacterial infectious disease or male infertility due to sperm abnormality.

2. The pharmaceutical composition of claim 1, wherein the disease is a prion-related disease.

3. The pharmaceutical composition of claim 1, wherein the disease is a bacterial infectious disease.

4. The pharmaceutical composition of claim 1, wherein the disease is male infertility due to sperm abnormality.

5. A mutant angiotensin-converting enzyme (ACE) consisting of the amino acid sequence of SEQ ID NO: 4 except Glu at position 414 is substituted with Asp.

* * * * *

SEQUENCE LISTING

```
<160> NUMBER OF SEQ ID NOS: 4

<210> SEQ ID NO 1
<211> LENGTH: 37
<212> TYPE: DNA
<213> ORGANISM: Artificial Sequence
<220> FEATURE:
<223> OTHER INFORMATION: description of artificial sequence: Synthetic
      oligonucleotide

<400> SEQUENCE: 1
tgaattccac catgggccaa ggttgggcta ctccagg                           37

<210> SEQ ID NO 2
<211> LENGTH: 57
<212> TYPE: DNA
<213> ORGANISM: Artificial Sequence
<220> FEATURE:
<223> OTHER INFORMATION: description of artificial sequence: Synthetic
      oligonucleotide

<400> SEQUENCE: 2
gaattcgtca cttatcatca tcatccttat aatcctgctg tggctccagg tacaggc     57
```

-continued

```
<210> SEQ ID NO 3
<211> LENGTH: 48
<212> TYPE: DNA
<213> ORGANISM: Artificial Sequence
<220> FEATURE:
<223> OTHER INFORMATION: description of artificial sequence: Synthetic
      oligonucleotide

<400> SEQUENCE: 3
cttggtgata gcgcaccacg atatgggcca catccagtat ttcatgca                    48

<210> SEQ ID NO 4
<211> LENGTH: 764
<212> TYPE: PRT
<213> ORGANISM: Mus musculus
<300> PUBLICATION INFORMATION:
<308> DATABASE ACCESSION NUMBER: GenPept/NP_033728
<309> DATABASE ENTRY DATE: 2003-10-04

<400> SEQUENCE: 4
```

Met Gly Gln Gly Trp Ala Thr Pro Gly Leu Pro Ser Phe Leu Phe Leu
1               5                   10                  15

Leu Leu Cys Cys Gly His His Leu Leu Val Leu Ser Gln Val Ala Thr
            20                  25                  30

Asp His Val Thr Ala Asn Gln Gly Ile Thr Asn Gln Ala Thr Thr Arg
        35                  40                  45

Ser Gln Thr Thr Thr His Gln Ala Thr Ile Asp Gln Thr Gln Ile
    50                  55                  60

Pro Asn Leu Glu Thr Asp Glu Ala Lys Ala Asp Arg Phe Val Glu Glu
65                  70                  75                  80

Tyr Asp Arg Thr Ala Gln Val Leu Leu Asn Glu Tyr Ala Glu Ala Asn
                85                  90                  95

Trp Gln Tyr Asn Thr Asn Ile Thr Ile Glu Gly Ser Lys Ile Leu Leu
            100                 105                 110

Glu Lys Ser Thr Glu Val Ser Asn His Thr Leu Lys Tyr Gly Thr Arg
        115                 120                 125

Ala Lys Thr Phe Asp Val Ser Asn Phe Gln Asn Ser Ser Ile Lys Arg
    130                 135                 140

Ile Ile Lys Lys Leu Gln Asn Leu Asp Arg Ala Val Leu Pro Pro Lys
145                 150                 155                 160

Glu Leu Glu Glu Tyr Asn Gln Ile Leu Leu Asp Met Glu Thr Thr Tyr
                165                 170                 175

Ser Leu Ser Asn Ile Cys Tyr Thr Asn Gly Thr Cys Met Pro Leu Glu
            180                 185                 190

Pro Asp Leu Thr Asn Met Met Ala Thr Ser Arg Lys Tyr Glu Glu Leu
        195                 200                 205

Leu Trp Ala Trp Lys Ser Trp Arg Asp Lys Val Gly Arg Ala Ile Leu
    210                 215                 220

Pro Phe Phe Pro Lys Tyr Val Glu Phe Ser Asn Lys Ile Ala Lys Leu
225                 230                 235                 240

Asn Gly Tyr Thr Asp Ala Gly Asp Ser Trp Arg Ser Leu Tyr Glu Ser
                245                 250                 255

Asp Asn Leu Glu Gln Asp Leu Glu Lys Leu Tyr Gln Glu Leu Gln Pro
            260                 265                 270

Leu Tyr Leu Asn Leu His Ala Tyr Val Arg Arg Ser Leu His Arg His
        275                 280                 285

Tyr Gly Ser Glu Tyr Ile Asn Leu Asp Gly Pro Ile Pro Ala His Leu

-continued

```
            290                 295                 300
Leu Gly Asn Met Trp Ala Gln Thr Trp Ser Asn Ile Tyr Asp Leu Val
305                 310                 315                 320

Ala Pro Phe Pro Ser Ala Pro Asn Ile Asp Ala Thr Glu Ala Met Ile
                325                 330                 335

Lys Gln Gly Trp Thr Pro Arg Arg Ile Phe Lys Glu Ala Asp Asn Phe
            340                 345                 350

Phe Thr Ser Leu Gly Leu Leu Pro Val Pro Pro Glu Phe Trp Asn Lys
        355                 360                 365

Ser Met Leu Glu Lys Pro Thr Asp Gly Arg Glu Val Val Cys His Pro
    370                 375                 380

Ser Ala Trp Asp Phe Tyr Asn Gly Lys Asp Phe Arg Ile Lys Gln Cys
385                 390                 395                 400

Thr Ser Val Asn Met Glu Asp Leu Val Ile Ala His His Glu Met Gly
                405                 410                 415

His Ile Gln Tyr Phe Met Gln Tyr Lys Asp Leu Pro Val Thr Phe Arg
            420                 425                 430

Glu Gly Ala Asn Pro Gly Phe His Glu Ala Ile Gly Asp Ile Met Ala
        435                 440                 445

Leu Ser Val Ser Thr Pro Lys His Leu Tyr Ser Leu Asn Leu Leu Ser
    450                 455                 460

Thr Glu Gly Ser Gly Tyr Glu Tyr Asp Ile Asn Phe Leu Met Lys Met
465                 470                 475                 480

Ala Leu Asp Lys Ile Ala Phe Ile Pro Phe Ser Tyr Leu Ile Asp Gln
                485                 490                 495

Trp Arg Trp Arg Val Phe Asp Gly Ser Ile Thr Lys Glu Asn Tyr Asn
            500                 505                 510

Gln Glu Trp Trp Ser Leu Arg Leu Lys Tyr Gln Gly Leu Cys Pro Pro
        515                 520                 525

Val Pro Arg Ser Gln Gly Asp Phe Asp Pro Gly Ser Lys Phe His Val
    530                 535                 540

Pro Ala Asn Val Pro Tyr Val Arg Tyr Phe Val Ser Phe Ile Ile Gln
545                 550                 555                 560

Phe Gln Phe His Glu Ala Leu Cys Arg Ala Ala Gly His Thr Gly Pro
                565                 570                 575

Leu His Lys Cys Asp Ile Tyr Gln Ser Lys Glu Ala Gly Lys Leu Leu
            580                 585                 590

Ala Asp Ala Met Lys Leu Gly Tyr Ser Lys Pro Trp Pro Glu Ala Met
        595                 600                 605

Lys Leu Ile Thr Gly Gln Pro Asn Met Ser Ala Ser Ala Met Met Asn
    610                 615                 620

Tyr Phe Lys Pro Leu Thr Glu Trp Leu Val Thr Glu Asn Arg Arg His
625                 630                 635                 640

Gly Glu Thr Leu Gly Trp Pro Glu Tyr Asn Trp Ala Pro Asn Thr Ala
                645                 650                 655

Arg Ala Glu Gly Ser Thr Ala Glu Ser Asn Arg Val Asn Phe Leu Gly
            660                 665                 670

Leu Tyr Leu Glu Pro Gln Gln Ala Arg Val Gly Gln Trp Val Leu Leu
        675                 680                 685

Phe Leu Gly Val Ala Leu Leu Val Ala Thr Val Gly Leu Ala His Arg
    690                 695                 700

Leu Tyr Asn Ile Arg Asn His His Ser Leu Arg Arg Pro His Arg Gly
705                 710                 715                 720
```

```
Pro Gln Phe Gly Ser Glu Val Glu Leu Arg His Ser Leu Ala His Arg
            725                 730                 735

Leu Tyr Asn Ile Arg Asn His His Ser Leu Arg Arg Pro His Arg Gly
            740             745                 750

Pro Gln Phe Gly Ser Glu Val Glu Leu Arg His Ser
        755                 760
```